United States Patent [19]

Postley

[11] Patent Number: 4,940,728
[45] Date of Patent: Jul. 10, 1990

[54] TREATMENT FOR SINO-NASAL CONGESTION

[76] Inventor: John E. Postley, 17 E. 89th St., New York, N.Y.

[21] Appl. No.: 735,482

[22] Filed: May 17, 1985

[51] Int. Cl.$^5$ .............................................. A61K 31/34
[52] U.S. Cl. ................................................... 514/474
[58] Field of Search ........................... 514/476; 424/45

[56] References Cited

U.S. PATENT DOCUMENTS

| | | | |
|---|---|---|---|
| 3,039,929 | 6/1962 | Stanko | 514/474 X |
| 3,215,602 | 11/1965 | Diamond | 514/474 |
| 4,251,563 | 2/1981 | Gruetzmacher et al. | 514/474 X |
| 4,525,341 | 6/1985 | Deihl | 514/474 X |

OTHER PUBLICATIONS

Chemical Abstracts 74: 67698e (1971).

*Primary Examiner*—Leonard Schenkman
*Attorney, Agent, or Firm*—Brumbaugh, Graves, Donohue & Raymond

[57] ABSTRACT

A method for the treatment of allergic rhinitis, headaches commonly referred to as "sinus headaches" and other afflictions of the sino-nasal area comprising the administration of ascorbic acid and its salts in a pharmaceutically acceptable liquid carrier to the nasal mucosa.

5 Claims, No Drawings

4,940,728

TREATMENT FOR SINO-NASAL CONGESTION

BACKGROUND OF THE INVENTION

The present invention relates to a method of treatment for allergic rhinitis, "sinus headaches," viral nasopharyngitis, and other afflictions of the sino-nasal area associated with nasal congestion.

The discomfort associated with nasal congestion is substantial, and the headache produced when the congestion occludes the openings of the paranasal sinuses into the nasal cavity can be unbearable. Besides severe pain, the occlusion of these openings can lead to the inoculation of the occluded congested tissues with bacteria. This can lead to acute abscesses of the sinuses and to chronically infected sinuses which may lead to progressive asthma and respiratory insufficiency as well as pain and disability. Clearly a safe and effective means of reducing the congestion of these tissues and preventing the cycle of disease that might result is needed.

The traditional methods for the treatment of allergic rhinitis and nasal congestion all have well known side effects. Antihistamines cause drowsiness and can impair judgment in the use of automobiles and other machinery. Decongestants, and adrenalin derivatives, may elevate blood pressure, cause palpitations of the heart and impair the patient's ability to sleep. Topical vasoconstrictor nasal preparations allow a rebound phenomenon as they wear off, resulting in increased nasal congestion. In the long-acting form, topical vasoconstrictors can cause an atrophic thinning of the lining tissues of the nose if topical nasal treatment is continued over too long a period.

There are also two classes of prescription topical nasal preparations available: (1) adrenal steroids and (2) cromolyn sodium solution. Adrenal steroid ("cortisone") derivatives are effective. On long term use, however, they result in a fragility of the tissues to which they are applied which results in bleeding and a propensity to yeast infections. Cromolyn sodium solution is expensive but also effective for many although not all cases of nasal congestion.

With an understanding of the limitations of the available treatments for nasal congestion, it is apparent that an inexpensive method of treatment which does not have local and systemic toxic effects, would provide a novel and beneficial addition to the available therapeutic treatments. The benefits would be even more apparent if the treatment would, in addition, provide relief for those patients who are not helped by the traditional modalities of treatment, their side effects notwithstanding.

Ascorbic acid (Vitamin C) is a well-known organic chemical. It is stable in dry form although it is sensitive to heat (leading to oxidation) and there is a gradual darkening of the solid on exposure to light. It is also sensitive to acids and alkalis when in solution and is known to deteriorate rapidly in the presence of copper, iron and silver. There have been numerous claims that when taken orally, Vitamin C is effective in the prevention of viral nasopharyngitis ("the common cold"), but test results have been inconclusive on this point. Similarly, there have been claims made for its efficacy in the prevention of certain forms of bronchial asthma when taken orally. These claims were not substantiated, however, when ascorbic acid was given intravenously before allergic inhalation challenges. Thus, the actual efficacy of ascorbic acid in treating these conditions, and the mechanism by which the observed effects are produced, is unclear.

There are several patents relating to the topical use of ascorbic acid (U.S. Pat. Nos. 3,954,989; 3,920,848; 4,424,232), which refer specifically to the application of a combination of substances including Vitamin C to the skin. These patents relate to the soothing, anesthetic or healing properties of combinations including ascorbic acid. None of these patents, however, provides for the application of the ascorbic acid to the nasal mucous membrane and none makes reference to the anti-allergic or topical decongestant effect of ascorbic acid on IgA secreting mucous membrane.

SUMMARY OF THE INVENTION

A method for treatment of allergic rhinitis, headaches commonly referred to as "sinus headaches," viral nasopharyngitis, and other congestive afflictions of the sinonasal tissues has been found comprising applying a solution comprising ascorbic acid, or a salt, or an ester of ascorbic acid, alone or in combination, dissolved in a pharmaceutically acceptable liquid carrier to the nasal mucosa in an amount effective to treat sino-nasal congestion.

DETAILED DESCRIPTION OF THE INVENTION

The present invention relates to the novel use of solutions of ascorbic acid, its salts and esters in a pharmaceutically acceptable liquid carrier to be topically administered to the nasal mucosa for the purpose of the treatment of allergic rhinitis, headaches commonly referred to as "sinus headaches," and congestive afflictions of the sinonasal tissues. This method has been found to produce a prompt decrease in nasal congestion, with no demonstrable side effects, and no tendency for rebound congestion. In addition, reduction of nasal congestion by application of this method leads to reduction of the duration and the severity of viral nasopharyngitis.

According to the present invention, ascorbic acid, sodium ascorbate, other salts of ascorbic acid, esters of ascorbic acid, or combinations of these compounds are dissolved in a pharmaceutically acceptable liquid carrier at a concentration of about 0.4% to 3.0% by weight. This ascorbate containing solution is then applied topically to the nasal mucosa. It should be noted that the unadjusted pH of ascorbic acid in water is about 3.0 and produces an unpleasant stinging sensation to the nose when applied. This makes a solution of the acid alone in water less desirable. The preferred pH is between 6 and 8. The most preferred pH is about 7.8 which produces no noxious stimulation to the mucosa and has generally been reported to be without taste. A pH of 7.8 is obtained when sodium ascorbate is dissolved in water. The pH of a solution can be adjusted as needed by the addition of acid, such as HCl, or base, such as NaOH.

The pharmaceutically acceptable liquid carrier used in preparing the ascorbate solution is preferably water, but other liquids, such as propylene glycol, are also usable. In fact, any liquid which is non-toxic to the nasal mucosa and which dissolves ascorbic acid, its salts or esters would be a suitable carrier. Since heat, light, and contact with possible trace mineral contaminants in tap water hasten the discoloration of the solution, the solution should be kept away from light and in a cool place after it has been made up preferably in a pure liquid carrier such as distilled water. An effective solution can, nevertheless, be made up in tap water but the solution will have a shortened useful life. In some applications, it may be desirable to use a sterile carrier.

The ascorbate solution may optionally contain additional ingredients including other medications, pharmaceutically acceptable flavorants or odorants, and pharmaceutically acceptable buffering agents to maintain the pH at an acceptable level (6–8) for application. Examples of suitable odorants include oil of wintergreen, oil or orange, and eucalyptus extract.

Once prepared, the solution can be administered into the nose in the form of drops or spray or any other method which allows for topical application to the nasal mucosa. The treatment can be repeated every two to three hours as necessary to obtain relief. No more that two applications per day are usually necessary for the average patient and in treating sinus headaches applications may be as infrequent as once or twice a week. The following examples are set forth to illustrate the invention.

EXAMPLE 1

200 mg. of pharmaceutical grade sodium ascorbate without preservatives was dissolved into 15 cc. of distilled water in a 30 cc. amber glass bottle with a dropper incorporated into the cap of the bottle. A dropperful (0.5 cc.) of the solution was introduced into each nostril of a supine patient suffering from nasal congestion due to allergic rhinitis. Nasal congestion was relieved. The treatment was repeated twice daily to maintain the relief obtained with the initial instillation.

EXAMPLE 2

400 mg. of pharmaceutical grade sodium ascorbate without preservatives was dissolved into 15 cc. of distilled water in a plastic bottle with a nasal spray mechanism incorporated into the cap of the bottle. This spray was administered to a 49 year-old woman who had suffered from chronic frontal headaches extending as well to the bridge of the nose. The patient experienced relief of the headache within 15 minutes. The treatment was repeated on the average of once a week to maintain relief.

EXAMPLE 3

200 mg. of pharmaceutical grade sodium ascorbate without preservatives was dissolved into 15 cc. of distilled water in a 30 cc. amber glass bottle with a dropper incorporated into the cap of the bottle. A dropperful (0.5 cc.) of the solution was introduced into each nostril of a 74 year-old man suffering from progressive nasal congestion and hoarseness due to a viral nasopharyngitis. Treatment was continued every two hours during the day and at bedtime. Within 24 hours, the patient had an almost complete resolution of his symptoms.

The mechanism whereby this method of administering ascorbic acid acts to relieve nasal congestion is not known, however, it is hypothesized that it acts by inhibiting the secretory IgA antibody system. There is ample evidence that there is a liberal sprinkling of IgA secreting immunocytes throughout the nasal and paranasal sinus tissue, the lining tissues of the bronchial airways, and the gut from the stomach through the colon. It is known that the secretory IgA antibody is made at the mucosal surface and the antibody does not traverse the serum.

Thus far, the only experimental work on sensitization of the secretory IgA system has been done via the gut. It has been demonstrated that oral sensitization will produce secretory IgA antibody in the colostrum of the lactating human mother and in the bronchial secretions of mice and rats. There is experimental work which also demonstrates an anamnestic (memory) IgA response in the gut which does not require direct stimulation of the particular tissue to result in the re-appearance of an antibody at that site. This suggests that there is some humoral (hormonal) mechanism by which the physically discontinuous IgA mucosal system can communicate with itself. There is the possibility that this humoral agent may reach a threshold level with excess stimulation which could precipitate and perpetuate the asthmatic or nasal congestion response in the susceptible individual.

The effectiveness of ascorbic acid in relieving congestion when applied topically, but not intravenously, might be because it inhibits the ongoing secretion of the humoral agent by which the IgA system communicates with itself. Therefore, the action of ascorbic acid in alleviating the symptoms of the common cold would not be by a general stimulation of the immune system, but rather by reducing the concentration of a substance that causes congestion in mucosal surfaces generally. Thus, the topical application of the ascorbic acid directly to the nasal surface would have the more concentrated effect of inhibiting the allergic and congestive response without having its effect diluted by application to a remote surface. This mechanism would also explain the difficulty in demonstrating the effect of ascorbic acid on the common cold in scientific double-blind studies since these have never been controlled to determine the pre-existing allergic state of the participants.

I claim:

1. A method of treating sino-nasal congestion, viral nasopharyngitis, allergic rhinitis, and related conditions associated with nasal congestion comprising applying to the nasal mucosa a solution comprising ascorbic acid, a pharmaceutically acceptable salt or ester of ascorbic acid, or combinations thereof dissolved in a pharmaceutically acceptable liquid carrier in an amount effective to treat sino-nasal congestion.

2. A method according to claim 1, wherein the solution is applied in drops into each nostril 3. A method according to claim 1, wherein the solution is applied as an aerosol into each nostril.

4. A method according to claim 1, wherein the liquid carrier is water adjusted to a pH of about 7.8.

5. A method according to claim 4, wherein the solution contains about 0.4% to 3.0% by weight of sodium ascorbate dissolved in water.

* * * * *